(12) United States Patent
King et al.

(10) Patent No.: US 10,369,088 B2
(45) Date of Patent: Aug. 6, 2019

(54) PHOTOSENSITIZER BASED MICROSPHERES

(71) Applicant: INTERNATIONAL BUSINESS MACHINES CORPORATION, Armonk, NY (US)

(72) Inventors: Scott B. King, Rochester, MN (US); Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/459,517

(22) Filed: Mar. 15, 2017

(65) Prior Publication Data
US 2018/0263868 A1    Sep. 20, 2018

(51) Int. Cl.
| | | |
|---|---|---|
| *A61Q 17/04* | (2006.01) | |
| *A61K 8/11* | (2006.01) | |
| *A61K 8/02* | (2006.01) | |
| *A61K 8/81* | (2006.01) | |
| *A61K 8/35* | (2006.01) | |
| *A61K 8/37* | (2006.01) | |
| *A61K 8/40* | (2006.01) | |

(52) U.S. Cl.
CPC .............. *A61K 8/11* (2013.01); *A61K 8/025* (2013.01); *A61K 8/35* (2013.01); *A61K 8/37* (2013.01); *A61K 8/40* (2013.01); *A61K 8/8152* (2013.01); *A61Q 17/04* (2013.01); *A61K 2800/413* (2013.01); *A61K 2800/56* (2013.01)

(58) Field of Classification Search
CPC ............ A61Q 17/04; A61K 8/11; A61K 8/35
See application file for complete search history.

(56) References Cited

U.S. PATENT DOCUMENTS

| | | | |
|---|---|---|---|
| 6,238,650 B1 | 5/2001 | Lapidot et al. | |
| 7,993,677 B2 | 8/2011 | Ding et al. | |
| 8,828,464 B2 | 9/2014 | Atkin et al. | |
| 2002/0064541 A1 | 5/2002 | Lapidot et al. | |
| 2004/0105826 A1 | 6/2004 | Soane et al. | |
| 2009/0041691 A1* | 2/2009 | Candau | A61K 8/11 424/60 |

(Continued)

FOREIGN PATENT DOCUMENTS

WO     2014/132261 A2    9/2014

OTHER PUBLICATIONS

"The Trouble with Oxybenzone and Other Su Chemicals" EWG's Guide to Sunscreens, http://www.ewg.org/sunscreen/report/the-trouble-with-sunscreen-chemicals/, accessed on Sep. 8, 2016, pp. 1-9.

(Continued)

*Primary Examiner* — Carlos A Azpuru
(74) *Attorney, Agent, or Firm* — Tutunjian & Bitetto, P.C.; Nathan Rau (57) ABSTRACT

An encapsulated sunscreen composition that includes a polymeric shell material having a substantially spherical geometry. The shell material is a polymeric composition that includes a photosensitizer chemically bound to the polymeric composition. The polymeric shell material has a minimum diameter of 100 nm.

20 Claims, 6 Drawing Sheets

(56) References Cited

U.S. PATENT DOCUMENTS

2010/0040696 A1  2/2010  Sente et al.
2015/0036234 A1  2/2015  Ben-Yakar et al.

OTHER PUBLICATIONS

Baker, "Ultrafast Photochemistry of Sunscreens" published on Jul. 16, 2016 by the University of Warwick, UK, on URL https://www2.warwick.ac.uk/fac/sci/moac/people/students/2013/lewis_baker/phd/ultrafast_photochemistry_sunscreens/, pp. 1-4.

* cited by examiner

2,4,6-trihydroxybenzoic acid 2,3,6-trihydroxybenzoic acid

Octinoxate microcapsule

FIG. 10A homosalate/octisalate microcapsule

FIG. 10B

Oxybenzone microcapsule

FIG. 10C

Octocrylene microcapsule

FIG. 10D

PHOTOSENSITIZER BASED MICROSPHERES

BACKGROUND

Technical Field

The present disclosure generally relates to sunscreen formulations, and more particularly to forming encapsulated sunscreen products.

Description of the Related Art

Sunscreens are products combining several ingredients that help prevent the sun's ultraviolet (UV) radiation from reaching the skin. Two types of ultraviolet radiation, i.e., UVA and UVB, damage the skin, age it prematurely, and increase the risk of skin cancer. It is believed that UVB is the principle form of radiation behind sunburn, while UVA rays, which penetrate the skin more deeply, are associated with wrinkling, leathering, sagging, and other light-induced effects of aging. The most common sunscreens on the market contain chemical filters that include a combination of two to six of the following active ingredients: oxybenzone, avobenzone, octisalate, octocrylene, homosalate, and octinoxate. One problematic chemical that is used in sunscreen is oxybenzone, found in nearly every chemical sunscreen. In some instances, oxybenzone can penetrate the skin, cause allergic skin reactions, and may disrupt hormones. It has also been determined that there may be a link between higher concentrations of oxybenzone and its metabolites in the human body and increased risk of endometriosis and lower birthweight. Further, oxybenzone has been implicated as a major contributor to the bleaching of coral reefs worldwide. Consequently, a need exists to mitigate the harmful effects of oxybenzone while maintaining its beneficial UV filtering properties.

SUMMARY

In accordance with an aspect of the present disclosure, an encapsulated sunscreen product is provided. In one embodiment, the encapsulated sunscreen product includes a polymeric shell material having a substantially spherical geometry, wherein the shell material comprises a polymeric composition comprising a photosensitizer chemically-bound to the polymeric composition. The polymeric composition has a minimum diameter of 100 nm.

In accordance with another aspect of the present disclosure, a sunscreen lotion is provided. The sunscreen lotion may include a lotion that includes an active ingredient comprising an encapsulated sunscreen product of a shell material having a substantially spherical geometry. The shell material includes a polymeric composition comprising a photosensitizer chemically-bound to the polymeric composition. The sunscreen lotion further includes a lotion liquid base containing the active ingredient mixed therein.

In accordance with another embodiment of present disclosure, a method of forming a sunscreen product is provided. The method may include forming a polyhydroxylate of a photosensitizer selected from the group consisting of oxybenzone, avobenzone, octisalate, octocrylene, homosalate, octinoxate and combinations thereof; and creating an aqueous solution including a polymeric wall forming material. The aqueous solution including the polymeric wall forming material may be mixed with the polyhydroxylate of the photosensitizer in combination with at least one of urea ($CH_4N_2O$), ammonia chloride ($NH_4Cl$), and resorcinol to provide an emulsion. The method may continue with adding a core agent to the emulsion, in which the wall forming material encapsulates the core agent to provide a shell material having a substantially spherical geometry with a polymeric composition having a chemically-bound photosensitizer.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The present disclosure generally relates to sunscreen formulations. The active ingredients of sunscreen formulations are either in the form of chemically active ingredients or physically active ingredients. Absorption of these active ingredients, if absorbed into the human body, such as during the application and use of the sunscreen formulations, can cause a number of health hazards. In some instances, chemically active ingredients, such as oxybenzone, avobenzone, octisalate, octocrylene, homosalate, and octinoxate have been bound to nanoparticles to limit their ability to be absorbed by the human body. Nanoparticles have also been used in first generation mineral sunscreens, but similar to cosmetics applications, the use of nanoparticles can create regulatory challenges due to a number of factors that include, but are not limited to their size, shape, surface area, and coating compositions. The methods, compositions, and structures described herein provide a novel route to ensure that chemical filters are not absorbed through the skin. In some embodiments, a microsphere approach is described herein that does not involve binding of the chemical filters to nanoparticles. In some embodiments, the microsphere approach that is described herein prevents skin absorption due to the size of the microspheres. For example, the microspheres provided herein have a minimum size of 100 nm, i.e., the microspheres including the chemical filters may have a size of 100 nm or greater. The methods, compositions, and structures described herein bind photosensitizer, e.g., chemical filtering agents, such as oxybenzone, avobenzone, octisalate, octocrylene, homosalate, and octinoxate, with and/or to the shell of the polymeric microsphere. This is distinguishable from encapsulating a photosensitizer, e.g., chemical filtering agent, as the core of a sphere structure. In some embodiments, by bonding the photosensitizer with/to the shell, the chemical agent is not free to release and potentially absorb into the skin due to the macromolecular scaling of the polymeric shell material. As will further be described below, the core of the microsphere may incorporate additional features and health serving purposes. In some embodiments, the core of the microsphere may include oils and fragrances. In some other embodiments, the core may be composed of natural compounds that benefit/promote skin health, natural product extracts, etc.

Figure 1:
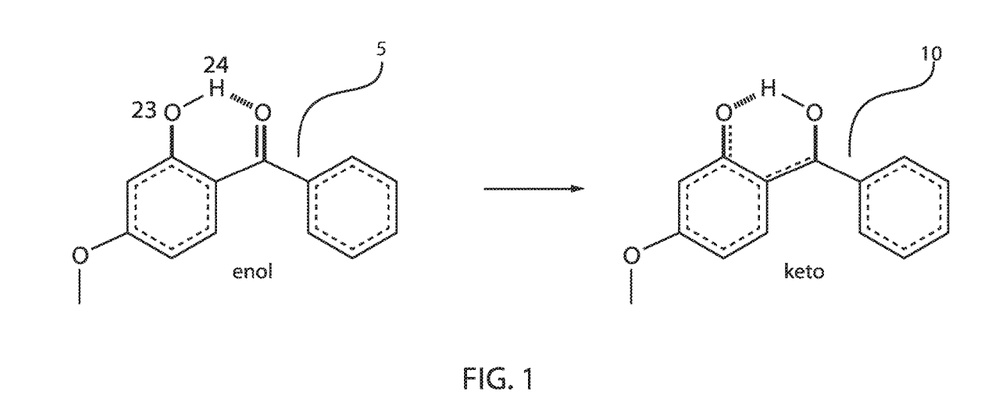
FIG. 1 is a chemical structure diagram illustrating one embodiment of excited state enol to keto tautomerization that is consistent with absorbing UVA/B sunlight, in accordance with an embodiment of the present disclosure.

Most common sunscreens on the market contain chemical filters, which can include a combination of two to six of the following active ingredients: oxybenzone, avobenzone, octisalate, octocrylene, homosalate, and octinoxate. Chemical filters function by absorbing UVA/B sunlight and converting it to vibrational energy. In some embodiments, in which the chemical filter is provided by oxybenzone, the photoprotective properties can be understood in terms of an initial ultrafast excited state enol (identified by reference number 5) to keto (identified by reference number 10) tautomerization, as depicted in FIG. 1. This is followed by efficient internal conversion, and subsequent vibrational relaxation to the ground state (enol) tautomer. The same photochemical principals also apply to octisalate and homosalate photosensitizer molecules in this disclosure.

Figure 2:
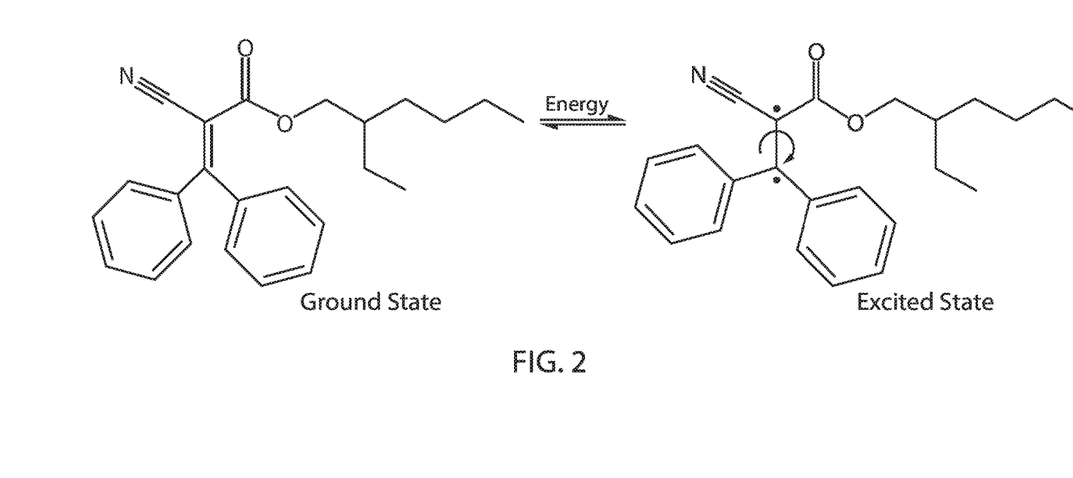
FIG. 2 is a chemical structure diagram illustrating one embodiment of the photochemical reaction of octocrylene functioning as a chemical filter, in accordance with one embodiment of the present disclosure.

FIG. 2 illustrates the photochemical reaction of octocrylene functioning as a chemical filter. The photochemical reaction of octocrylene takes place by the absorption of UV light by the ground state molecule that results in the excited state formation of a diradical from an electron pair of the central double bond 11, 11a. A diradical is a molecular species with two electrons occupying two degenerate molecular orbitals. This diradical is short lived and relaxes back to the low energy, double bond state.

The methods, compositions and structures described herein provide for derivitizing oxybenzone, avobenzone, octisalate, octocrylene, homosalate, octinoxate or analogous compounds to utilize a microsphere approach that allows for binding the photosensitizer to the shell material. The microspheres having the photosensitizer bound thereto posses a large enough size and chemical compatibility, resulting in the prevention of the microspheres being absorbed into living tissue. For example, the size of the microsphere capsule is large enough to be an obstruction to dermal absorption by humans, i.e., the absorption of the microspheres through the skin, i.e., living tissue, of a human being. In some embodiments, the microencapsule described herein may have a diameter that is greater than 100 nm. In one embodiment, the microcapsule provided herein may have a diameter ranging from 100 nm to 20 microns. In other embodiments, the microencapsule described herein may have a diameter ranging from 500 nm to 10 microns. In yet further embodiments, the microcapsule provided herein may be on the order of 1 micron to 5 microns. It is noted that the above example ranges are provided for illustrative purposes only, and that other sizes and ranges may also be possible. In other examples, the microcapsule having the chemical filter bound to a polymeric shell composition may have a diameter equal to 500 nm, 550 nm, 600 nm, 650 nm, 700 nm, 750 nm, 800 nm, 850 nm, 900 nm, 950 nm, 1 microns, 2 microns, 3 microns, 5 microns, 6 microns, 7 micron, 8 microns, 9 microns, 10 microns, 11 microns, 12 microns, 13 microns, 14 microns, 15 microns, 16 microns, 17 microns, 18 microns, 19 microns and 20 microns, as well as any range of diameters including an upper value provided by one of the aforementioned examples, and a lower value provided by one of the aforementioned examples.

In some embodiments, the methods for forming the microspheres including a shell having a chemical filtering agent bound thereto or within may begin with the forming of a polyhydroxylated derivative of at least one of oxybenzone, avobenzone, octisalate, octocrylene, homosalate, and octinoxate. A polyhydroxylated derivative contains two or more hydroxyl groups per molecule. The polyhydroxylated derivative may be synthesized or purchased from a commercial source.

Figure 3:
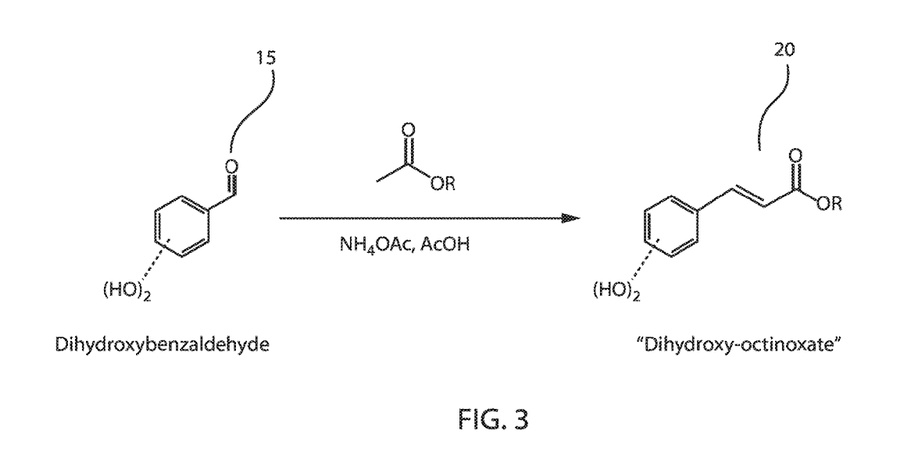
FIG. 3 is a chemical reaction illustrating one embodiment of synthesis of polyhydroxylated octinoxate analog, in accordance with one embodiment of the present disclosure.
Figure 4A:
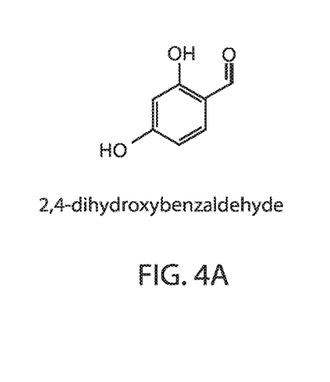
FIG. 4A is a chemical structure diagram for 2,4-dihydroxybenzaldehyde, which can provide one embodiment of a precursor in the synthesis of polyhydroxylated octinoxate analog.
Figure 4B:
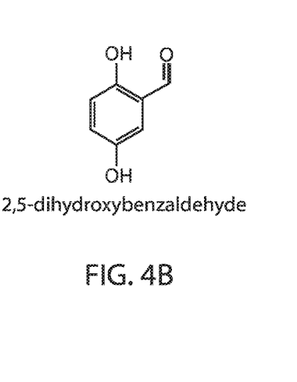
FIG. 4B is a chemical structure diagram for 2,5-dihydroxybenzaldehyde, which can provide one embodiment of a precursor in the synthesis of polyhydroxylated octinoxate analog.
Figure 4C:
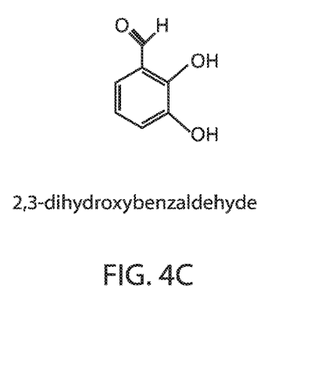
FIG. 4C is a chemical structure diagram for 2,3-dihydroxybenzaldehyde, which can provide one embodiment of a precursor in the synthesis of polyhydroxylated octinoxate analog.

Referring to FIG. 3, in one embodiment, the polyhydroxylated octinoxate derivative 20 is prepared by a condensation reaction with an alkyl acetate (typically 2-(ethyl)hexylacetate). A condensation reaction is a chemical reaction in which two molecules or moieties, often functional groups, combine to form a larger molecule, together with the loss of a small molecule. For example, a precursor 15, such as dihydroxybenzaldehyde, may be reacted with a mixture of 2-(ethyl)hexylacetate in a mixture with a solvent/buffer solution, such as a mixture of acetic acid (AcOH) and ammonium acetate ($NH_4OAc$). Acetic acid is a chemical compound with the formula $CH_3CO_2H$. Ammonium acetate is a chemical compound with the formula $NH_4CH_3CO_2$. The R group depicted in FIG. 3 may be 2-ethylhexyl. It is noted that the precursor 15 is not limited to only the chemical composition that is depicted in FIG. 3. For example, other precursor 15 compositions may be suitable for use in the reaction depicted in FIG. 3, such as 2,4-dihydroxybenzaldehyde (as depicted in FIG. 4A), 2,5-dihydroxybenzaldehyde (as depicted in FIG. 4B), and 2,3-dihydroxybenzaldehyde (as depicted in FIG. 4C). Further, 2-(ethyl)hexylacetate is not the only alkyl acetate that is suitable for reaction with the aforementioned precursors to provide the polyhydroxylated octinoxate derivative 20. Other alky acetates that are suitable for use in the reaction depicted in FIG. 3 may include methyl acetate, ethyl acetate, n-propyl acetate, isopropyl acetate, n-butyl acetate and isobutyl acetate.

Figure 5:
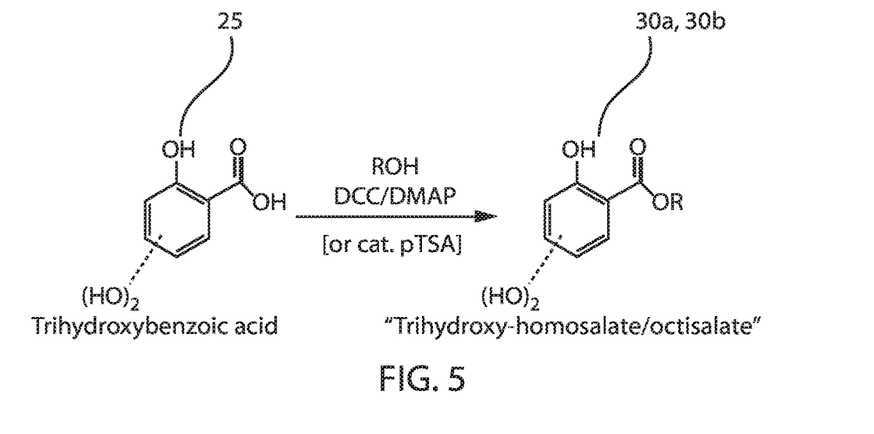
FIG. 5 is a chemical reaction illustrating one embodiment of synthesis of a polyhydroxylated octisalate analog, in accordance with one embodiment of the present disclosure.

Referring to FIG. 5, polyhydroxylated homosalate derivative 30a and octisalate derivative 30b are prepared from the trihydroxybenzoic acids 25 by esterification with either 2-(ethyl)hexanol in the case of polyhydroxylated octisalate 30b, and 3,3,5-trimethylcyclohexanol in the case of polyhydroxylated homosalate 30a. In the chemical equation depicted in FIG. 5, the R group is 2-ethylhexyl for the octisalate analog. In the chemical equation depicted in FIG. 5, the R group is 3,3,5-Trimethylcyclohexyl for the homosalate analog. When the precursor, i.e., trihydroxybenzoic acid 25, is reacted with 2-ethylhexanol (abbreviated 2-EH), the product is a trihydroxyoctisalate; when the precursor, i.e., trihydroxybenzoic acid 25, is reacted with 3,3,5-trimethylcyclohexanol, the product is a trihydroxyhomosalate. The chemical formula of 2-ethylhexanol is $C_8H_{18}O$; 3,3,5-trimethylcyclohexanol has the chemical formula $C_9H_{18}O$.

Figure 6A:
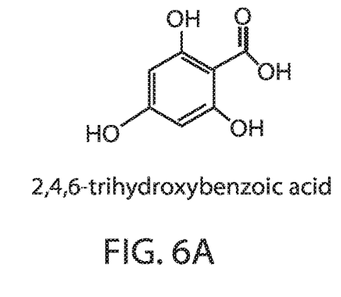
FIG. 6A is a chemical structure diagram for 2,4,6-trihydroxybenzoic acid, which can provide one embodiment of a precursor in the synthesis of polyhydroxylated octisalate analog.
Figure 6B:
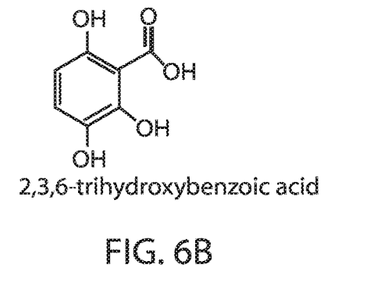
FIG. 6B is a chemical structure diagram for 2,3,6-trihydroxybenzoic acid, which can provide one embodiment of a precursor in the synthesis of polyhydroxylated octisalate analog.

It is noted that 2-(ethyl)hexanol and 3,3,5-trimethylcyclohexanol are not the only examples of precursors that may be employed for forming the polyhydroxylated octisalate derivative 30a and homosalate derivative 30b, respectively, using reactions similar to those depicted in FIG. 3. Other chemical compositions, e.g., acids, suitable for use as the precursor for forming the polyhydroxylated homosalate derivative 30a and octisalate derivative 30b may include hydroxybenzoic acid, such as 2,4,6-trihydroxybenzoic acid and 2,3,6-trihydroxybenzoic acid. FIG. 6A is a chemical structure diagram for 2,4,6-trihydroxybenzoic acid, which can provide one embodiment of a precursor in the synthesis of a polyhydroxylated octisalate derivative. FIG. 6B is a chemical structure diagram for 2,3,6-trihydroxybenzoic acid, which can provide one embodiment of a precursor in the synthesis of another polyhydroxylated octisalate derivative.

In some embodiments, the esterification process includes the formation of esters, wherein esters are produced when carboxylic acids are heated with alcohols in the presence of an acid catalyst. The catalyst is usually concentrated sulphuric acid. Dry hydrogen chloride gas is used in some cases. In the reaction depicted in FIG. 5, the acid catalyst may be provided by p-toluenesulfonic acid (PTSA or pTsOH) or tosylic acid (TsOH). P-toluenesulfonic acid (PTSA or pTsOH) or tosylic acid (TsOH) is an organic compound with the formula $CH_3C_6H_4SO_3H$. Other acid catalysts that may be substituted for P-toluenesulfonic acid (PTSA) include benzenesulfonic acid and sulfanilic acid.

In other embodiments, the esterification process can include Steglich esterification. Steglich esterification is a variation of an esterfication with dicyclohexylcarbodiimide (i.e., N,N'-dicyclohexylcarbodiimide (DCC)) as a coupling reagent and 4-dimethylaminopyridine (DMAP) as a catalyst. This reaction generally takes place at room temperature, e.g., 20° C. to 25° C. A suitable solvent for this type of esterification includes dichloromethane.

Figure 7:
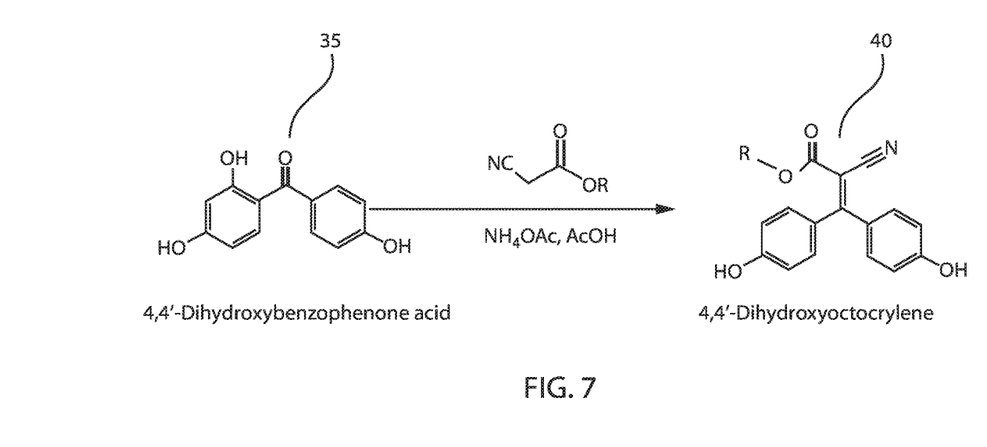
FIG. 7 is a chemical reaction illustrating one embodiment of synthesis of a dihydroxyoctocrylene analog, in accordance with one embodiment of the present disclosure.
Figure 8A:
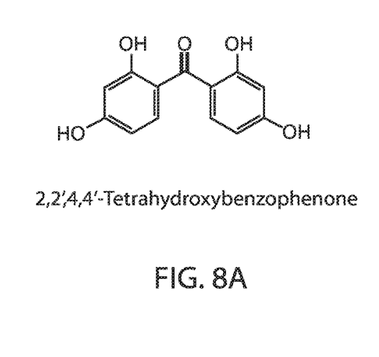
FIG. 8A is a chemical structure diagram for 2, 2', 4, 4'-tetrahydroxybenzophenone, which can provide one embodiment of a precursor in the synthesis of dihydroxyoctocrylene analog.
Figure 8B:
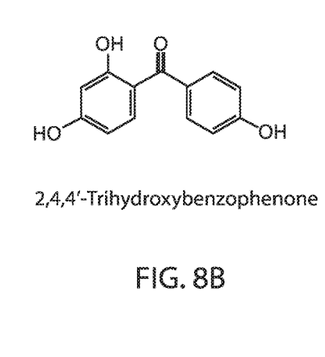
FIG. 8B is a chemical structure diagram for 2, 4, 4'-trihydroxybenzophenone acid, which can provide one embodiment of a precursor in the synthesis of dihydroxyoctocrylene analog.

FIG. 7 is a chemical reaction illustrating one embodiment of the synthesis of a dihydroxyoctocrylene analog. In the chemical reaction depicted in FIG. 7, the R group is 2-ethylhexyl. Dihydroxyoctocrylene derivative 40 can be prepared from a precursor 35, such as dihydroxybenzophenone, via a condensation with an alkyl carbonocyanidate (typically R=2-ethylhexyl). One example of dihydroxybenzophenone that may provide the precursor for the reaction depicted in FIG. 7 includes 4,4'-Dihydroxybenzophenone. Other examples of benzophenones that may provide the precursor for the reaction depicted in FIG. 7 may include 2, 2', 4, 4'-tetrahydroxybenzophenone, as depicted in FIG. 8A, or 2, 4, 4'-trihydroxybenzophenone acid, as depicted in FIG. 8B.

It is noted that the above described examples of polyhydroxylated compounds of oxybenzone, avobenzone, octisalate, octocrylene, homosalate, octinoxate and combinations thereof have been provided for illustrative purposes, and it is not intended that the present disclosure be only limited to these examples, as other examples of polyhydroxylated compounds are also within the scope of the present disclosure. For example, while not shown here, a multitude of other possible structural analogues to the polyhydroxylated octocrylene and oxybenzones in FIGS. 3-8 that have hydroxyl groups at other positions. These can be prepared via Friedel-Crafts acylation reactions, aldol condensation reactions, enolate additions reactions, or enolate condensation reactions of various hydroxybenzoyl chloride and hydroxybenzene derivatives. Friedel-Crafts acylation includes an electrophilic aromatic substitution that allows for the synthesis of monoacylated products from reactions between arenes and acyl chlorides or anhydrides. The products are deactivated, and typically do not undergo a second substitution. In some instances, a stoichiometric amount of the Lewis acid catalyst is required, because both the substrate and the product form complexes. An aldol condensation is a condensation reaction in in which an enol or an enolate ion reacts with a carbonyl compound to form a β-hydroxyaldehyde or β-hydroxyketone. This is followed by dehydration to give a conjugated enone. An aldol is basically a class of enolate additions followed by condensation. The present disclosure is not limited to only this example.

Figure 9:
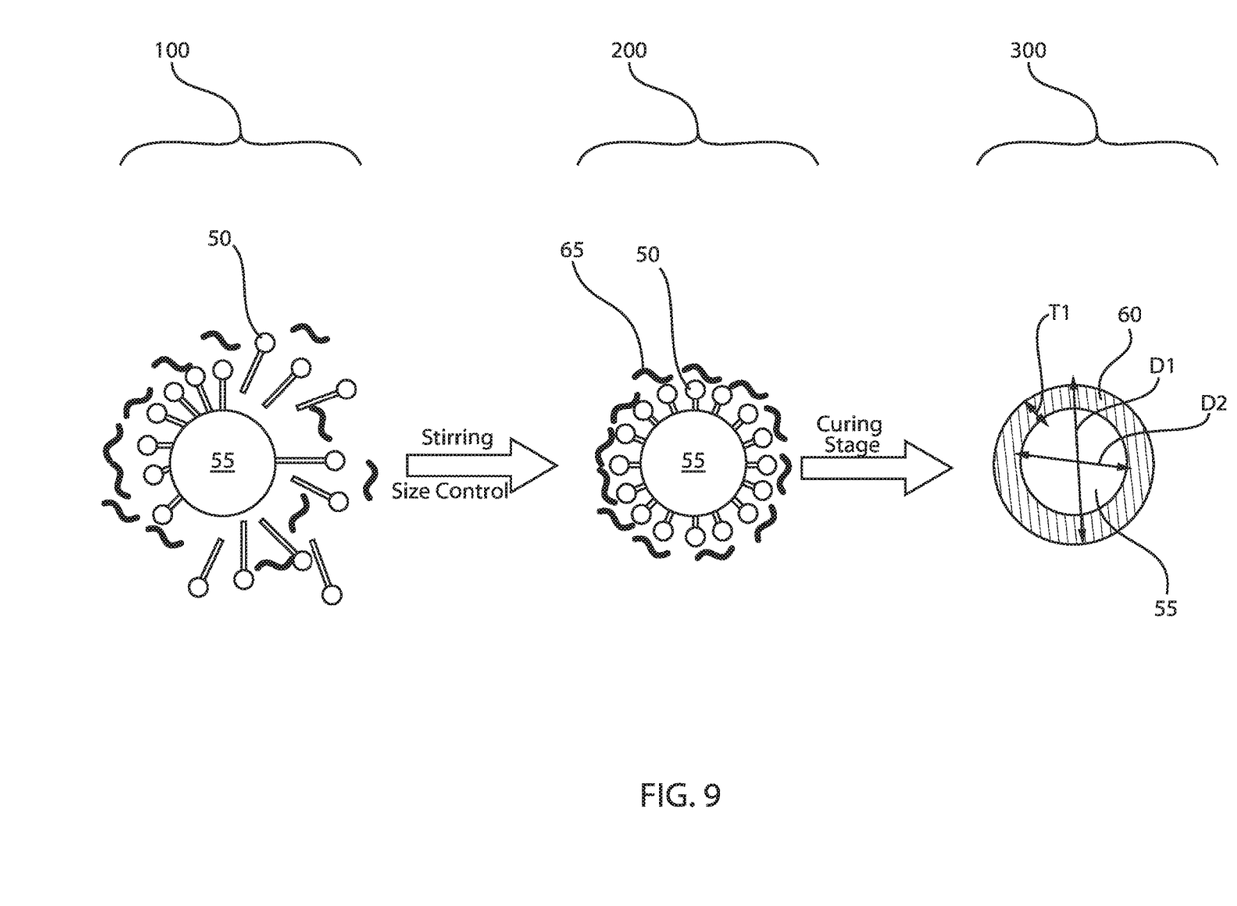
FIG. 9 is an illustration depicting one process flow for forming micro capsules having chemically active ingredients, such as analogous of oxybenzone, avobenzone, octisalate, octocrylene, homosalate, and octinoxate, bound to the polymeric shell of the microencapsule.

The photosensitizer containing microspheres are then prepared from the polyhydroxylated compounds. FIG. 9 is an illustration depicting one process flow for forming microcapsules having chemically active ingredients, such as oxybenzone, avobenzone, octisalate, octocrylene, homosalate, and octinoxate, bound to/within the polymeric shell of the microcapsule.

Microcapsules were prepared by in situ polymerization in an oil-in-water emulsion. In some embodiments, forming the microcapsules may include the steps of mixing a polymeric wall forming element containing solution with a polyhydroxylated oxybenzone, avobenzone, octisalate, octocrylene, homosalate, octinoxate, or combination of the aforementioned polyhydroxylated compositions. The solution is mixed to create a homogenous solution 100. In a following process step, the homogenous mixture is mixed with an aqueous solution containing an emulsifier, under low shear stirring, to thereby form an emulsion 200. Thereafter, the method continuous with adding to the formed emulsion an amount of water which initiates extraction of the organic solvent from the emulsion, thereby obtaining micro capsules. The final process step further includes curing 300.

In some embodiments, forming the photosensitizer containing microspheres includes adding the polyhydroxylated compounds, e.g., polyhydroxylated oxybenzone, avobenzone, octisalate, octocrylene, homosalate, octinoxate, or combination of the aforementioned polyhydroxylated compositions, to a wall forming polymer 50. The phrase "wall-forming polymer", which is also referred to herein as "wall-forming polymeric material" refers to a polymeric material (e.g., a polymer or copolymer) or a combination of two or more different polymeric materials, as defined herein, which form a component of the external wall or layer or shell of the microcapsules 500. The term "polymer shell" 60 also refers to a polymer layer comprised of the wall-forming polymer(s). As noted above, the oxybenzone, avobenzone, octisalate, octocrylene, homosalate, octinoxate, or combination of the aforementioned polyhydroxylated compositions are bound to the polymer shell 60, or are bound within the polymer shell.

In one embodiment, the polymer shell 60 is provided by ethylene-(methyl acrylate) (EMA) copolymer, but the polymer component that is mixed with polyhydroxylated compounds of oxybenzone, avobenzone, octisalate, octocrylene, homosalate, octinoxate and combinations thereof is not limited to only this example. Other polyacrylate polymers and other polymeric compositions are suitable for providing the polymer shell, i.e., the wall forming polymeric 50 material that provides the polymer shell 60. For example, the composition of the polymer shell 60 that is mixed with the polyhydroxylated compounds of oxybenzone, avobenzone, octisalate, octocrylene, homosalate, octinoxate and combinations thereof may be a polyacrylate, a polymethacrylate, a cellulose ether or ester, or any combination thereof. In some embodiments, the wall-forming polymeric material 50 comprises ammonium methacrylate copolymer type B (poly (ethyl acrylate)-co-(methyl methacrylate)-co-(trimethylammonium-ethyl methacrylate chloride), also known as Eudragit RSPO or EuRSP0).

In some embodiments, the wall forming polymer 50 is mixed with the polyhydroxylated compounds of oxybenzone, avobenzone, octisalate, octocrylene, homosalate, octinoxate and combinations thereof in an aqueous solution. For example, an aqueous solution, e.g., 100 ml aqueous solution, including the polymer composition, e.g., EMA copolymer, may be formed, in which the polymer composition is present in an amount ranging from 1 wt. % to 10 wt. %. In other examples, the aqueous solution, e.g., 100 ml aqueous solution, of the polymer composition, e.g., EMA copolymer, may be formed, in which the polymer composition is present in an amount ranging from 2 wt. % to 5 wt. %. The aqueous solution may be mixed, e.g., mechanically, at a rate of 500 rpm to 1500 rpm, e.g., 1000 rpm. The aqueous suspension may be maintained at room temperature (20-24° C.), in which a vessel containing the solution can be suspended in a temperature-controlled water bath.

The polyhdroxylated photosensitizer, as depicted in FIGS. 3-8, may be added to the stirring aqueous solution containing the wall forming copolymer 50, e.g., EMA copolymer, in combination with urea ($CH_4N_2O$), and ammonia chloride ($NH_4Cl$). The urea may be added in amounts ranging from $5 \times 10^{-2}$ mol to 0.1 mol, the ammonium chloride may be added in amounts ranging from $7 \times 10^{-2}$ mol to 0.12 mol, and the polyhydroxylated photosensitizer may be added in amount ranging from $2 \times 10^{-2}$ mol to $6 \times 10^{-2}$ mol. Resorcinol can also be dissolved in the solution including the wall forming copolymer, e.g., EMA copolymer, in which the resorcinol is added to the solution in combination with the wall forming copolymer, urea and ammonia chloride. Resorcinol (or resorcin) is a benzenediol (m-dihydroxybenzene) having the formula $C_6H_6O_2$. In some embodiments, the resorcinol can be omitted, because the modified photosensitizers act as resorcinol-like molecules. When incorporated, resorcinol may be included in amounts similar to the amounts provided for the above described photosensitizers, so long as the combination of the resorcinol and photosensitizer does not exceed the maximum allowance for the photosensitizer.

In some examples, the solution can be agitated with a mixer for dissolving the photosensitizer, ammonium chloride, resorcinol, and urea. The mixer may be a digital mixer, such as digital mixer (Eurostar, IKA Labortechnik) driving a three-bladed, 63.5 mm diameter low-shear mixing propeller (Cole Parmer), which may operate at this stage of the process flow at a rate of 500 rpm to 1500 rpm, e.g., 1000 rpm. It is noted that in some embodiments, the size of the micro capsules including the polymer shell 60 including the photosensitizer compositions bound thereto may be impacted by the rate and time period of stirring.

The addition of sodium hydroxide (NaOH) and hydrochloric acid (HCl) may be used to adjust the pH from a first value ranging from 2.4 to 2.8, e.g., 2.6, to a second value ranging 3.25 to 3.75, e.g., 3.50. In addition to sodium hydroxide and hydrochloric acid, other pH adjusting agents may include, for example, one or more of adipic acids, glycines, citric acids, calcium hydroxides, magnesium aluminometasilicates, buffers or any combinations thereof.

In some examples, when necessary n-octanol, e.g., 1-octanol, may be added, e.g., dropwise, to eliminate surface bubbles.

In a following process step, a core agent 55 may be added to form an emulsion. In embodiments, the core agent 55 may be composed of an oil or fragrance. In some other embodiments, the core agent 55 may be composed of natural compounds that benefit/promote skin health, natural product extracts, etc.

The wall forming polymer 50 reacts with the urea and the formaldehyde at the aforementioned adjusted PH to form an encapsulating wall, i.e., polymer shell 60 around the core agent 55. Additionally, the polyhdroxylated chemical filtering agents, such as oxybenzone, avobenzone, octisalate, octocrylene, homosalate, and octinoxate, are bound with and/or to the shell of the polymeric shell 60 of the microsphere capsule 500. In some embodiments, the EMA copolymer acts as a surfactant to form the micelle. The oil moves to the inside of the micelle, and forms the oil-in-water emulsion. Once the oil-in-water emulsion is formed, the reaction can proceed to then generate the urea-formaldehyde polymer. The addition of ammonium chloride decreases the pH of the system. The decrease in pH of the system is due to the reaction between ammonium chloride and formaldehyde, and more so due to the reaction between ammonium chloride and hydroxymethyl urea. In addition to reducing the pH of the system, the reaction between ammonium chloride and urea-formaldehyde resin can generate surface active substances, which can help to drive the formation of the microcapsules. Polymerization can be catalyzed by either acid or base, the precipitous drop in pH leads to a rapid increase in polymerization rate Further emulsifiers that could facilitate the formation of the core shell structures that provide the microencapsulated spheres, in which photosynthesizer, e.g., chemical filtering agents, such as oxybenzone, avobenzone, octisalate, octocrylene, homosalate, and octinoxate, are bound with and/or to the polymer shell 60 of the polymeric microsphere, may include sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Formaldehyde is used in the polymer urea-formaldehyde microcapsules. In some examples, after stabilization, an aqueous solution of formaldehyde can be added to the emulsion. Formaldehyde is a naturally occurring organic compound with the formula $CH_2O$ (H—CHO). The addition of the formaldehyde completes the encapsulation process, and in some instances hardens the polymeric shell 60. The final step in the preparation of the microspheres is the addition of the formaldehyde, which acts as a curing agent to complete the polymeric shell formation 60.

In some embodiments, the emulsion is covered and heated at a rate of about 1° C. per min to the target temperature that is above room temperature, e.g., greater than 30° C. In some embodiments, the target temperature may range from 40° C. to 50° C. In one example, the temperature of the emulsion is heated to 55° C. In some examples, during the above described heating step, the emulsion may be continuously stirred, i.e., agitated, for a time period ranging from 1 hour to 24 hours. As the agitation rate is increased, a finer emulsion is obtained and the average microcapsule diameter decreases. Microcapsules with average diameter in the range of 10-1000 mm are obtained by adjusting agitation rate between 200-2000 rpm. After sufficient curing of the microcapsules, the emulsion is allowed to cool. Once cooled to ambient temperature, the suspension of microcapsules can be separated under vacuum with a coarse-fritted filter. In some embodiments, the microsphere capsules 300 were rinsed with deionized water and air dried for 24 to 48 hours. A sieve was used to aid in separation of the microsphere capsules 300.

In another embodiments, the above described reactions may be performed under UV-light to first induce the photochemical reaction that protects the photosensitizers ability to react as normal in a sunscreen formulation. Without this condition, some of the new derivatives discussed above could end up bonding through the hydroxyl group that is needed to undergo photochemical reaction.

The microsphere capsules 300 may each include a polymeric shell 60 and a core 55. The microsphere capsules 300 are substantially spherical. The diameter D1 of the microsphere capsules 300 is greater than 100 nm. In one embodiment, the microsphere capsules 300 provided herein may have a diameter D1 ranging from 100 nm to 20 microns. In other embodiments, the micro capsules described herein may have a diameter ranging from 500 nm to 10 microns. In yet further embodiments, the microsphere capsules 300 provided herein may be on the order of 1 micron to 5 microns. It is noted that the above example ranges are provided for illustrative purposes only, and that other sizes and ranges may also be possible. In other examples, the microsphere capsules 300 having the polymeric shell 60 bound to a chemical filter composition may have a diameter equal to 500 nm, 550 nm, 600 nm, 650 nm, 700 nm, 750 nm, 800 nm, 850 nm, 900 nm, 950 nm, 1 microns, 2 microns, 3 microns, 5 microns, 6 microns, 7 micron, 8 microns, 9 microns, 10 microns, 11 microns, 12 microns, 13 microns, 14 microns, 15 microns, 16 microns, 17 microns, 18 microns, 19 microns and 20 microns, as well as any range of diameters including an upper value provided by one of the aforementioned examples, and a lower value provided by one of the aforementioned examples.

As noted above, the polymeric shell 60 of the microsphere capsules 300 typically has a polyhydroxylated chemical filtering agents, such as oxybenzone, avobenzone, octisalate, octocrylene, homosalate, and octinoxate, that is bound with and/or to the polymeric component of the polymeric shell 60. The polyhydroxylated chemical filtering agents have been described above with reference to FIGS. 3-8. To provide the polymeric shell 60 the polyhydroxylated chemical filtering agents are reacted with a polymer or copolymer composition. For example, the polymer compositions that may be reacted with the polyhydroxylated chemical filtering agents to provide the polymeric shell 60 having the chemical filtering agent chemically bound thereto, such as through chemical bonding, may include ethylene-(methyl acrylate) (EMA) copolymer, polyacrylate, a polymethacrylate, a cellulose ether or ester, or any combination thereof.

Figure 10A:
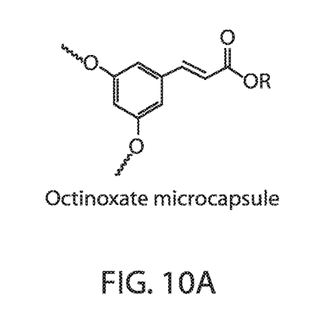
FIGS. 10A-10D are chemical structures illustrating the bonds of photosensitizers in final microcapsule materials.

In one embodiment, when the polyhydroxylated chemical filtering agent that is produced from the dihydroxy-octinoxate composition that is formed in accordance with the reaction described in FIG. 3 is reacted with ethylene-(methyl acrylate) (EMA) copolymer in accordance with the process flow described in FIG. 9, a microsphere capsule 300 is produced having a polymeric shell 60 with the chemical formula depicted in FIG. 10A.

Figure 10B:
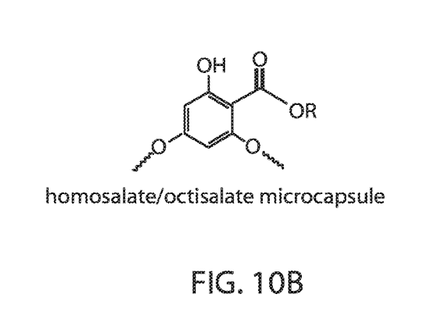

In another embodiment, when the polyhydroxylated chemical filtering agent that is produced from the trihydroxy-homosalatae/octisalate composition that is formed in accordance with the reaction described in FIG. 5 is reacted with ethylene-(methyl acrylate) (EMA) copolymer in accordance with the process flow described in FIG. 9, a microsphere capsule 300 is produced having a polymeric shell 60 with the chemical formula depicted in FIG. 10B.

In yet another embodiment, when the polyhydroxylated chemical filtering agent that is produced from the trihydroxy-homosalatae/octisalate composition that is formed in accordance with the reaction described in FIG. 5 is reacted with ethylene-(methyl acrylate) (EMA) copolymer in accordance with the process flow described in FIG. 9, a microsphere capsule 300 is produced having a polymeric shell 60 with the chemical formula depicted in FIG. 10B.

Figure 10C:
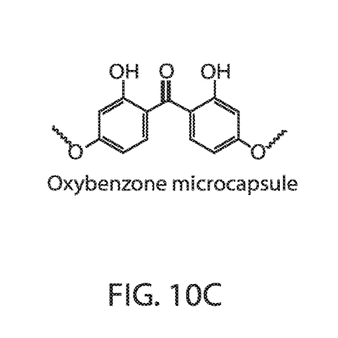

In a further embodiment, when the polyhydroxylated chemical filtering agent that is produced from the 4,4'-dihydroxy-octocrylene composition that is formed in accordance with the reaction described in FIG. 7 is reacted with ethylene-(methyl acrylate) (EMA) copolymer in accordance with the process flow described in FIG. 9, a microsphere capsule 300 is produced having a polymeric shell 60 with the chemical formula depicted in FIG. 10C.

Figure 10D:
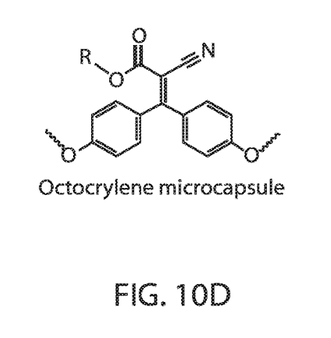

In an even further embodiment, when a polyhydroxylated chemical filtering agent includes octocrylene and is reacted with ethylene-(methyl acrylate) (EMA) copolymer in accordance with the process flow described in FIG. 9, a microsphere capsule 300 is produced having a polymeric shell 60 with the chemical formula depicted in FIG. 10D.

The dimensions of the diameter D1 of the polymeric shell 60 provides the greatest dimension of the microsphere capsule 300. In the methods, structures, and compositions disclosed herein, the diameter D1 is great enough to ensure that the microsphere capsule 300 is not absorbed by living tissue. In some embodiments, the thickness T1 of the polymeric shell also has a dimension that obstructs absorption by living tissue. In this instance, in the event that a microsphere capsule 300 is damaged or ruptured, the polymeric shell 60, which includes the polyhydroxylated chemical filtering agent, is not absorbed by living tissue. The thickness T1 of the polymeric shell 60 may range from 100 nm to 10 microns. In other embodiments, the thickness T1 of the polymeric shell 60 may range from 250 nm to 500 microns.

The centrally positioned core 55 of the microsphere capsules 300 may be composed of oils and fragrances. In some other embodiments, the centrally positioned core 55 may be composed of natural compounds that benefit/promote skin health, natural product extracts, etc. The core 55 may have a diameter ranging from 100 nm to 10 microns. In other embodiments, the micro capsules described herein may have a diameter ranging from 500 nm to 5 microns. It is noted that core 55 may include other ingredients, such as odorants, oils, anti-irritants, active agents etc. Suitable anti-irritants include, for example, steroidal and non-steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

Exemplary additional active agents that may be incorporated into the core 55 according to this embodiment of present invention include, without limitation, one or more, or any combination of an antibiotic agent, an antimicrobial agent, an anti-acne agent, an anti-aging agent, a wrinkle-reducing agent, a skin whitening agent, a sebum reducing agent, an antibacterial agent, an antifungal agent, an antiviral agent, a steroidal anti-inflammatory agent, a nonsteroidal anti-inflammatory agent, an anesthetic agent, an antipruritic agent, an antiprotozoal agent, an anti-oxidant, an antineoplastic agent, an immunomodulator, an interferon, an antidepressant, an anti histamine, a vitamin, a hormone, and an anti-dandruff agent.

Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives.

Suitable anti-acne agents for use in the core 55 can include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in the core 55 can include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that can be present within the core 55 can include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these nonsteroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents that may be used in the core 55 can include, without limitation, pharmaceutically acceptable salts of methdilazine and trimeprazine.

Non-limiting examples of anesthetic drugs that are suitable for use in the core 55 in accordance with the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in the core 55 of the micro capsules 300 include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the core 55 include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents useable within the core 55 include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, and XR9576.

Exemplary anti-dandruff agents for use within the core 55 may include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of vitamins that can be incorporated within the core 55 include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in the core 55 within context of the present invention include jojoba oil and aromatic oils such as methyl salicylate, wintergreen, peppermint oil, bay oil, *eucalyptus* oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

The core 55 may have a diameter D2 ranging from 100 nm to 10 microns. In other embodiments, the core 55 may have a diameter D2 ranging from 250 nm to 500 microns.

It is noted that the above core 55 compositions and core 55 dimensions are provided for illustrative purposes only, and are not intended to limit the present disclosure. Other core compositions have been contemplated that are solid compositions, liquid compositions or gas compositions.

The microspheres are then incorporated in sunscreen formulations. Any of the microsphere capsules 300 including a polymeric shell 60 having a chemical bound thereto that includes a polyhydroxylated chemical filtering agent, such as oxybenzone, avobenzone, octisalate, octocrylene, homosalate, and octinoxate, are within the scope of the present disclosure to be incorporated into sunscreen formulations. The sunscreen formulations suitable for use with the methods and compositions disclosed herein may include many combinations of synthetic and natural ingredients. A formulation is generally geared towards a specific SPF rating or the needs of a specific consumer group. Some embodiments employed herein include the above described microsphere capsules 300 for the active ingredient of the sunscreen, in which the microsphere capsules 300 including a polymeric shell 60 with a polyhydroxylated chemical filtering agents that may include a derivative of one of oxybenzone, avobenzone, octisalate, octocrylene, homosalate, and octinoxate chemically bound to the polymeric shell 60.

In addition to the sunscreening active ingredients, the formulations contemplated herein are typically emulsions such as lotions and creams, and therefore will contain several other components selected by the formulator from water, emulsifiers, emollients, fragrances, preservatives, vitamins, humectants, skin conditioners, antioxidants, waterproofing agents, and others. Antioxidants are often combined with titanium dioxide to slow down the oxidation of oils and thereby delay the deterioration of the lotion. Some examples of natural antioxidants are vitamins E and C, rice bran oil, and sesame seed oil. Another popular antioxidant in the natural category is green tea. Some sunscreen products also contain skin soothing and moisturizing additives such as aloe and chamomile.

Formulating the sunscreen lotion may begin with purifying water. Reverse osmosis extracts pure, fresh water by forcing water under pressure through a semipermeable membrane which separates pure water molecules from salts and other impurities. The active ingredients of the sunscreen lotion may then be mixed with the purified water. In some embodiments, the sunscreen lotion may be an emulsion that is formed by a process sequence that includes adding flake/powder ingredients to the oil being used to prepare the oil phase. The active ingredients may then be dispersed in the oil phase. The active ingredients may be the microsphere capsules 300, in which the microsphere capsules 300 includes a polymeric shell 60 with a polyhydroxylated chemical filtering agents that may include a derivative of one of oxybenzone, avobenzone, octisalate, octocrylene, homosalate, and octinoxate chemically-bound to the polymeric shell 60. A water phase containing emulsifiers and stabilizers may then be prepared. The oil (including the premixed active ingredients) and water may then be mixed to form an emulsion. Forming the emulsion can be aided by heating to between 110° F.-185° F. (45° C.-85° C.) depending on the formulation and viscosity desired. Mixing may be continued until the desired properties of the end product is provided.

Example—Prophetic Synthesis of Photosensitizer-Based Microspheres

To a 1000 mL beaker, deionized water (200.0 mL) and 2.5 or 5.0 wt % EMA copolymer solution (50 mL) were added and mixed at room temperature with a mechanical stirrer at 1000 rpm. The beaker was then suspended in an oil bath at room temperature. To this solution, urea (5 g, $8.32 \times 10^{-2}$ mol), ammonium chloride (0.5 g, $9.34 \times 10^{-3}$ mol) and photosensitizer ($4.54 \times 10^{-3}$ mol) are added and dissolved. The photosensitizer used included polyhydroxylated compounds of oxybenzone, avobenzone, octisalate, octocrylene, homosalate, octinoxate and combinations thereof. The pH was adjusted from 2.60 to 3.50 by addition of 10 wt % sodium hydroxide (NaOH) and concentrated hydrochloric acid (HCl). To eliminate surface bubbles, 1-octanol (1-2 drops) was added. A slow stream of core agent (60 mL) is then added and stirred for 10 min to form a stable emulsion. After stabilization, a 37 wt % formaldehyde solution (12.67 g, $4.22 \times 10^{-1}$ mol) was added to obtain a 1:1.9 molar ratio of formaldehyde to urea. The emulsion was then covered with aluminum foil and heated to 55° C. at a rate of 1° C./min. After 4 hours of continuous agitation at 1000 rpm, the mixer and hot plate are turned off and the emulsion is allowed to cool to ambient temperature. After cooling, the microspheres that were formed were isolated with a coarse-fritted filter. Microcapsules are then rinsed with deionized water (3×, 200 mL) and air dried for a time period ranging from 24 hours to 48 hours. The microcapsules formed by the present example had a diameter on the order of 30 microns.

Having described preferred embodiments of a composition and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims:

What is claimed is:
1. An encapsulated photosensitizer composition comprising:
a shell material having a substantially spherical geometry, wherein the shell material comprises a polymeric composition comprising a photosensitizer chemically-bound to the polymeric composition.
2. The encapsulate photosensitizer composition of claim 1, wherein the shell material has a minimum diameter of 100 nm.
3. The encapsulate photosensitizer composition of claim 1, wherein the photosensitizer comprises a polyhydroxylated composition selected from the group consisting of oxybenzone, avobenzone, octisalate, octocrylene, homosalate, octinoxate, and combinations thereof.
4. The encapsulate photosensitizer composition of claim 1, wherein the polymeric composition is a derivative of a polymer selected from the group consisting of ethylene-(methyl acrylate) (EMA) , polyacrylate, a polymethacrylate, a cellulose ether or ester, and a combination thereof.
5. The encapsulate photosensitizer composition of claim 1, wherein the shell material of the polymeric composition is entirely encapsulating a core material of an oil or fragrance.
6. The encapsulate photosensitizer composition of claim 1, wherein the core material is selected from the group consisting of anti-microbial compositions, anti-inflamatory compositions, odorants, oils, anti-irritant compositions, anti-aging compositions, anti-acne compositions, antibiotics and combinations thereof.
7. The encapsulate photosensitizer composition of claim 1, wherein the shell material has a thickness of 100 nm or greater.
8. A lotion comprising:
an active ingredient comprising an encapsulated photosensitizer composition of a shell material having a substantially spherical geometry, wherein the shell material comprises a polymeric composition comprising a photosensitizer chemically bound to the polymeric composition; and
a lotion liquid base containing the active ingredient mixed therein.
9. The lotion of claim 8, wherein the shell material has a minimum diameter of 100 nm, and the shell material has a thickness of 100 nm or greater.
10. The lotion of claim 8, wherein the photosensitizer comprises a polyhydroxylated composition selected from the group consisting of oxybenzone, avobenzone, octisalate, octocrylene, homosalate, octinoxate, and combinations thereof.
11. The lotion of claim 8, wherein the polymeric composition is a derivative of a polymer selected from the group consisting of ethylene-(methyl acrylate) (EMA) , polyacrylate, a polymethacrylate, a cellulose ether or ester, and a combination thereof.
12. The lotion of claim 8, wherein the shell material of the polymeric composition is entirely encapsulating a core material of an oil or fragrance.
13. The lotion of claim 8, wherein the core material is selected from the group consisting of anti-microbial compositions, anti-inflamatory compositions, odorants, oils, anti- irritant compositions, anti-aging compositions, anti-acne compositions, antibiotics and combinations thereof.
14. A method of forming a photosensitizer composition comprising:
forming a polyhydroxylate of a photosensitizer selected from the group consisting of oxybenzone, avobenzone, octisalate, octocrylene, homosalate, octinoxate and combinations thereof;
creating an aqueous solution including a polymeric wall forming material;

mixing the aqueous solution including the polyhydroxylate of the photosensitizer with the aqueous solution in combination with a polymeric shell forming material provide an emulsion; and adding a core agent to the emulsion, wherein wall forming material encapsulates the core agent to provide a shell material having a substantially spherical geometry with a polymeric composition having a chemically bound photosensitizer provided by said polyhydroxylate.

15. The method of claim 14, wherein the shell material has a minimum diameter of 100 nm, and the shell material has a thickness of 100 nm or greater.

16. The method of claim 15 further comprising mechanical mixing of said emulsion.

17. The method of claim 14, further comprising adjusting the PH to initiate encapsulation of the core material with the polymeric wall forming material.

18. The method of claim 14 further comprising adding formaldehyde to the emulsion to cure the shell material.

19. The method of claim 14, wherein the polymeric wall forming material is a polymer selected from the group consisting of ethylene-(methyl acrylate) (EMA), polyacrylate, a polymethacrylate, a cellulose ether or ester, and a combination thereof.

20. The method of claim 14, wherein the polymeric shell forming material comprises at least one of urea ($CH_4N_2O$), ammonia chloride ($NH_4C_1$), and resorcinol.

* * * * *